US010842445B2

(12) United States Patent
Wang et al.

(10) Patent No.: US 10,842,445 B2
(45) Date of Patent: Nov. 24, 2020

(54) SYSTEM AND METHOD FOR UNSUPERVISED DEEP LEARNING FOR DEFORMABLE IMAGE REGISTRATION

(71) Applicant: General Electric Company, Schenectady, NY (US)

(72) Inventors: Bo Wang, Schenectady, NY (US); Thomas Kwok-Fah Foo, Clifton Park, NY (US); Desmond Teck Beng Yeo, Clifton Park, NY (US); Jhimli Mitra, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 173 days.

(21) Appl. No.: 16/184,690

(22) Filed: Nov. 8, 2018

(65) Prior Publication Data

US 2020/0146635 A1    May 14, 2020

(51) Int. Cl.
*G06K 9/00* (2006.01)
*A61B 5/00* (2006.01)
*A61B 8/08* (2006.01)
*G06K 9/66* (2006.01)
*G06T 7/37* (2017.01)
(Continued)

(52) U.S. Cl.
CPC .......... *A61B 5/7267* (2013.01); *A61B 5/055* (2013.01); *A61B 5/7253* (2013.01); *A61B 8/08* (2013.01); *A61B 8/463* (2013.01); *A61B 8/483* (2013.01); *A61B 8/5261* (2013.01); *G01R 33/4814* (2013.01); *G01R 33/5608* (2013.01); *G06K 9/66* (2013.01); *G06T 7/37* (2017.01); *G06T 2207/10088* (2013.01);
(Continued)

(58) Field of Classification Search
CPC .................................................. G01R 33/4814
See application file for complete search history.

(56) References Cited

U.S. PATENT DOCUMENTS 8,233,681 B2   7/2012 Aylward et al.
8,620,055 B2   12/2013 Barratt et al.
(Continued)

OTHER PUBLICATIONS

Siddiqui, M. Minhaj, et al. "Comparison of MR/ultrasound fusion-guided biopsy with ultrasound-guided biopsy for the diagnosis of prostate cancer" JAMA 313.4 (2015): 390-397.
(Continued)

*Primary Examiner* — Avinash Yentrapati
(74) *Attorney, Agent, or Firm* — Fletcher Yoder, P.C.

(57) ABSTRACT

A method is provided. The method includes acquiring simultaneously multiple magnetic resonance (MR) images and multiple ultrasound images of an anatomical region of a subject over a scanned duration. The method also includes training an unsupervised deep learning-based deformable registration network. This training includes training a MR registration subnetwork based on the multiple MR images to generate MR deformation and transformation vectors, training an ultrasound registration subnetwork based on the multiple ultrasound images to generate ultrasound deformation and transformation vectors, and training a MR-to-ultrasound subnetwork based the multiple MR images and the multiple ultrasound images to generate MR-to-ultrasound deformation and transformation vectors between corresponding pairs of MR images and ultrasound images at each time point.

11 Claims, 4 Drawing Sheets

(51) Int. Cl.
*A61B 8/00* (2006.01)
*A61B 5/055* (2006.01)
*G01R 33/48* (2006.01)
*G01R 33/56* (2006.01)

(52) U.S. Cl.
CPC .............. *G06T 2207/10132* (2013.01); *G06T 2207/20048* (2013.01); *G06T 2207/30004* (2013.01)

(56) References Cited

U.S. PATENT DOCUMENTS

| | | | |
|---|---|---|---|
| 8,755,581 B2 | 6/2014 | Coupe et al. | |
| 2008/0247622 A1* | 10/2008 | Aylward | A61B 90/36 382/131 |
| 2010/0119135 A1* | 5/2010 | Coupe | G06K 9/32 382/131 |
| 2012/0155734 A1* | 6/2012 | Barratt | G06T 7/344 382/131 |
| 2014/0212014 A1* | 7/2014 | Kim | G06T 3/0068 382/131 |
| 2016/0210435 A1 | 7/2016 | Neumann et al. | |
| 2017/0014645 A1* | 1/2017 | Foo | A61B 8/5215 |
| 2017/0337682 A1* | 11/2017 | Liao | G06T 7/30 |
| 2018/0218516 A1 | 8/2018 | Reda et al. | |

OTHER PUBLICATIONS

Xu, Sheng, et al.; "Real-time MRI-TRUS fusion for guidance of targeted prostate biopsies", Computer Aided Surgery, vol. 13, Issue: 5, pp. 255-264, Sep. 2008.

Pinto, Peter A., et al.; "Magnetic resonance imaging/ultrasound fusion guided prostate biopsy improves cancer detection following transrectal ultrasound biopsy and correlates with multiparametric magnetic resonance imaging", The Journal of urology, vol. 186, Issue: 4, pp. 1281-1285, Oct. 2011.

Moradi, Mehdi, et al.; "Two solutions for registration of ultrasound to MRI for image-guided prostate interventions", Engineering in Medicine and Biology Society (EMBC), 2012 annual international conference of the IEEE. IEEE, pp. 1129-1132, 2012.

Liao, Rui, et al.; "An Artificial Agent for Robust Image Registration", Computer Vision and Pattern Recognition, pp. 9, Nov. 30, 2016.

De Vos, Bob, et al.; "End-to-end unsupervised deformable image registration with a convolutional neural network", Deep Learning in Medical Image Analysis and Multimodal Learning for Clinical Decision Support, pp. 204-212, Sep. 9, 2017.

Yang, Xiao, et al.; "Quicksilver: Fast predictive image registration—A deep learning approach", NeuroImage, vol. 158, pp. 24, Sep. 2017.

Balakrishnan, Guha, et al.; "An Unsupervised Learning Model for Deformable Medical Image Registration", Computer Vision and Pattern Recognition, pp. 9, 2018.

Yan, Pingkun, et al.; "Adversarial Image Registration with Application for MR and TRUS Image Fusion", Computer Vision and Pattern Recognition, pp. 8, 2018.

* cited by examiner

SYSTEM AND METHOD FOR UNSUPERVISED DEEP LEARNING FOR DEFORMABLE IMAGE REGISTRATION

BACKGROUND

The subject matter disclosed herein relates to image registration, and more particularly to systems and methods that utilize unsupervised deep learning in deformable image registration.

Magnetic resonance imaging (MRI) is becoming more important for guided intervention and therapy since it provides soft tissue contrast that enables mapping of the location and boundary of pathological tissue (e.g., tumors) in the planning/diagnosis phases. However, due to the limited patient space in the magnet bore and low imaging frame rate, it is difficult to integrate real-time MRI into interventional and therapy workflows. Thus, real-time MR images are typically not available in the interventional/treatment phase, which increases the risks of invasive access or treatment of healthy tissue regions that were not targeted in the planning phase. In addition, clinicians may fail to completely access or treat the pathological tissue due to the lack of real-time tracing of pathological tissue boundaries. While segmentation or manual tracing of a lesion/tumor from MR images in the planning phase may provide an initial location of the fiducial, due to physiological motion, this initial location may not be the true position of the target lesion/tumor.

Ultrasound imaging may provide real-time imaging. However, ultrasound imaging provides poorer soft tissue contrast, which limits the ability to locate or delineate pathology or target lesions. Linking real-time ultrasound imaging with pre-acquired MR images (acquired at a different time) is time-consuming, computationally intensive, and may have inaccuracies that adversely affects the precision and outcome of the intervention procedure. In addition, image contrast and spatial resolution in MRI and ultrasound imaging are different that exacerbates the difficulty in aligning or registering MRI and ultrasound images. Thus, there is a need for an imaging approach that provides sufficient soft tissue contrast during the intervention/treatment phase while also providing real-time positional information of the target lesion.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In a first embodiment, a method for providing real-time image guidance for an interventional procedure is provided. The method includes, prior to the interventional procedure: acquiring simultaneously a time-series magnetic resonance (MR) image set and a first time-series ultrasound image volume set in an MR imaging scanner from a patient that are matched at each time point; matching each MR image in the time-series MR image set in time to a corresponding ultrasound image volume in the first time-series ultrasound image set; performing an intermediate transformation to transfer lesion or structural anatomy contours acquired with other MR image contrast acquisition techniques to the time-series MR image set to complement the structural anatomical information available in the time-series MR image set; and for both the times series MR image set and the first times series ultrasound image volume set, respectively utilizing an MR image and a corresponding ultrasound image volume at some time point as a reference point in a respective MR reference image set and an ultrasound reference image set, calculating a respective first set of deformation and transformation vectors such that a position, a shape, an orientation, and a size of the object at the reference point matches that of the same object at a different time. The method also includes during the interventional procedure: acquiring a second time-series ultrasound image set such that at each time point the ultrasound images depict deformation of an anatomy-of interest of the patient as it varies in position, shape, orientation, or size over time; utilizing the second time-series ultrasound image set, calculating a second set of deformation and transformation vectors between the ultrasound images of the anatomy-of-interest at the current time point and the ultrasound images of the ultrasound reference image set at the reference point; applying the first and second sets of deformation and transformation vectors to the previously acquired MR images of the time-series MR image set to generate transformed MR images; displaying the transformed MR images as a representation of the true position, shape, and orientation of the anatomy-of-interest; and performing the interventional procedure using the transformed MR images for guidance.

In another embodiment, a method is provided. The method includes acquiring simultaneously multiple magnetic resonance (MR) images and multiple ultrasound images of an anatomical region of a subject over a scanned duration. The method also includes training an unsupervised deep learning-based deformable registration network. This training includes training a MR registration subnetwork based on the multiple MR images to generate MR deformation and transformation vectors, training an ultrasound registration subnetwork based on the multiple ultrasound images to generate ultrasound deformation and transformation vectors, and training a MR-to-ultrasound subnetwork based the multiple MR images and the multiple ultrasound images to generate MR-to-ultrasound deformation and transformation vectors between corresponding pairs of MR images and ultrasound images at each time point.

In a further embodiment, an interventional guidance system is provided. The system includes a memory encoding processor-executable routines. The system also includes a processing component configured to access the memory and to execute the processor-executable routines. The routines, when executed by the processing component, cause the processing component to receive multiple magnetic resonance (MR) images and a first multiple of ultrasound images of an anatomical region of a subject that were acquired simultaneously over a scanned duration prior to an interventional procedure. The routines, when executed by the processing component, also cause the processing component utilize the first plurality of ultrasound images and their corresponding MR images from the plurality of MR images to determine a MR-to-ultrasound transformation, and, then train an unsupervised deep learning-based deformable registration network to generate deformation and transformation vectors between ultrasound images from the plurality of ultrasound images from two time points to obtain an MR-to-ultrasound mapping via the deformation and transformation vectors and the MR-to-ultrasound transformation. The routines, when executed by the processing component, further cause the processing component to during the interventional procedure, receive a second multiple of ultrasound images of the anatomical region of the subject. The routines, when executed by the processing component, even further cause the processing component to utilize the trained unsupervised deep-learning based deformable registration network to determine secondary deformation and transformation vectors of the anatomical region between ultrasound images from the second multiple of ultrasound images at a current time point and reference ultrasound images from the first multiple of ultrasound images, to apply the MR-to-ultrasound deformation and transformation vectors to a reference MR image from the multiple MR images, and to subsequently apply the secondary deformation and transformation vectors to the reference MR image to generate a transformed MR image representative of the anatomical region at the current time point. The routines, when executed by the processing component, still further cause the processing component to display the transformed MR image during the interventional procedure.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Some generalized information is provided to provide both general context for aspects of the present disclosure and to facilitate understanding and explanation of certain of the technical concepts described herein.

Deep-learning approaches discussed herein may be based on artificial neural networks, and may therefore encompass deep neural networks, fully connected networks, convolutional neural networks (CNNs), perceptrons, auto encoders, recurrent networks, wavelet filter banks, or other neural network architectures. These techniques are referred to herein as deep-learning techniques, though this terminology may also be used specifically in reference to the use of deep neural networks, which is a neural network having a plurality of layers.

As discussed herein, deep-learning techniques (which may also be known as deep machine learning, hierarchical learning, or deep structured learning) are a branch of machine learning techniques that employ mathematical representations of data and artificial neural networks for learning and processing such representations. By way of example, deep-learning approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

As used herein, the term "virtual real-time MR image(s)" refers to the display of previously acquired MR images that correspond to a current state (e.g., respiratory state or position) of a patient or the anatomy-of-interest of a patient. Thus, displaying these MR images provides "real-time" MR imaging of the patient even though the current image modality being employed is ultrasound. By displaying the correct previously acquired MR images or set of MR images that accurately represents the positions of the anatomical structures within the imaging field-of-view, a system and process is described that enables real-time viewing of corresponding MR images when another imaging modality, such as ultrasound, is employed. Combining MR and real-time volumetric ultrasound imaging has the potential to provide clinicians with the soft-tissue image quality of MR images at the real-time frame rates of ultrasound.

The present disclosure systems and methods for utilizing an unsupervised deep learning-based fast deformable registration that can be applied to a wide range of interventional applications (e.g., radiation therapy, biopsy, surgical intervention, etc.) that utilize both MR and ultrasound images. Disclosed herein MR and ultrasound images are acquired simultaneously and utilized to train a neural network during a planning stage (prior to the interventional procedure). The neural network includes an ultrasound image (ultrasound-to-ultrasound) registration subnetwork, a MR image registration subnetwork, and a MR-to-ultrasound image transformation procedure. The MR-to-ultrasound image transformation procedure merges the registration of the ultrasound-to-ultrasound registration subnetwork and the MR image registration subnetwork together to enforce a consistency in estimated deformations. The ultrasound-to-ultrasound registration subnetwork allows the alignment or registration of ultrasound image volumes between any two time points. Taking into account information from the MR images enables a more accurate and robust image registration network for the ultrasound image registration. In the intervention phase, the trained ultrasound image registration subnetwork can be utilized to register ultrasound images acquired at the current time where a change may have occurred in the anatomy-of-interest (e.g., due to physiological motion or patient shifting). These real-time ultrasound images may be linked to the pre-acquired MR images via registering them to the ultrasound images acquired at planning stage and utilized to transform the images for display to provide real-time image guidance during the interventional procedure. The disclosed embodiments provide the soft tissue contrast advantage of MR and the real-time imaging capabilities of ultrasound.

Figure 1A:
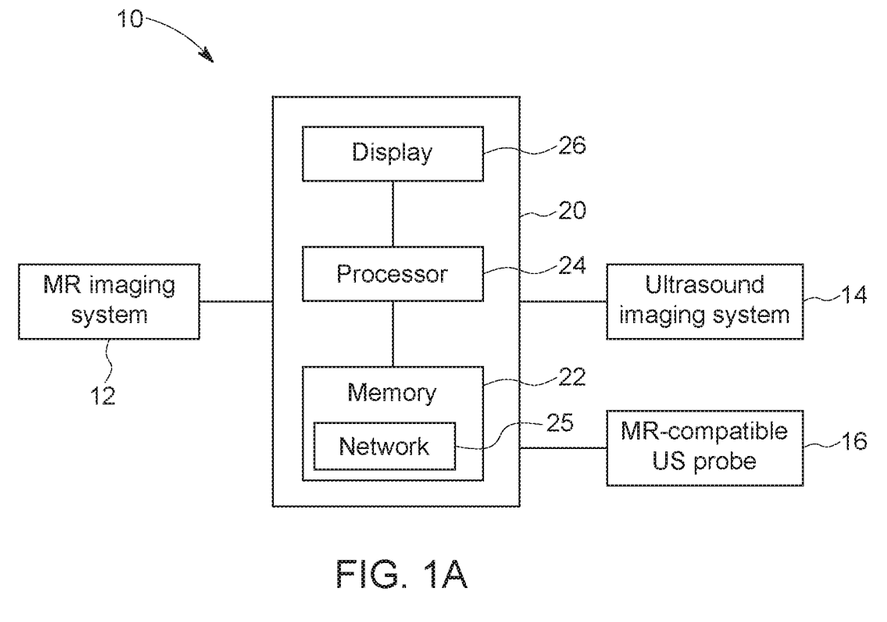
FIGS. 1A and 1B illustrate schematic diagrams of an embodiment of a combined magnetic resonance (MR) and ultrasound imaging system, in accordance with aspects of the present disclosure.
Figure 1B:
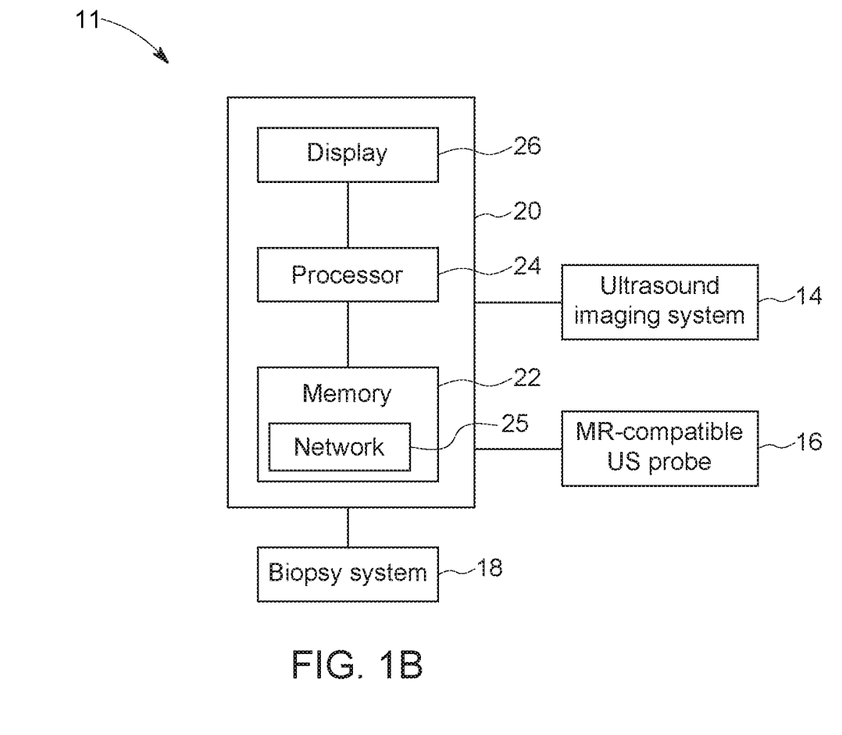

With the preceding comments in mind, FIG. 1A and FIG. 1B illustrate a schematic diagram of an embodiment of a combined MR and ultrasound imaging system 10 that may be used for non-invasive motion management of radiation therapy, or other therapy or surgical or interventional procedures, as described herein. The combined MR and ultrasound imaging system 10 may be similar to the system described in U.S. patent application Ser. No. 15/870,519, entitled "Image-guided Biopsy Techniques", filed Jan. 12, 2018, which may be incorporated by reference in its entirety. The combined MR and ultrasound imaging system 10 includes a magnetic resonance (MR) imaging system 12 and an ultrasound imaging system 14. The ultrasound imaging system 14 may be communicatively coupled to a MR-compatible ultrasound probe 16. The MR-compatible ultrasound probe 16 may be an ultrasound probe configured for use in combination with the MR imaging system 12. As such, the MR-compatible ultrasound probe (as described in U.S. patent application Ser. No. 15/897,964, entitled "Magnetic Resonance Compatible Ultrasound Probe", filed Feb. 15, 2018, which may be incorporated by reference in its entirety) may contain low or no ferromagnetic material (e.g., iron, nickel, cobalt) content, as discussed in greater detail with reference to FIG. 1. The system for image-guided intervention has two components. The first is a combined MR and ultrasound imaging system 10 that includes an ultrasound imaging system 14, and an MR-compatible ultrasound imaging probe 16 as depicted in FIG. 1A. It is also noted that in order to facilitate a more simple workflow, the ultrasound probe 16 is capable of three-dimensional (3D) volume acquisition with high temporal resolution, allowing an ultrasound image volume to be acquired at each time point. Moreover, besides being MR-compatible, the 3D ultrasound probe 16 is electronically steerable and hands-free. This allows the ultrasound image field-of-view to be electronically manipulated, obviating the need for robotic or mechanical ultrasound probe holders to change the imaging field-of-view. In this manner, simultaneous MR and ultrasound images can be easily acquired. Moreover, during the interventional procedure, the same ultrasound probe can be used and positioned in approximately the same manner as during the pre-interventional MR+ ultrasound procedure without difficulty. This provides a further simplification of the workflow as approximately the same imaging set up is used between the pre-interventional and interventional procedure as the same ultrasound probe is utilized, and in the same manner.

The data from the MR and ultrasound systems are streamed and stored in a memory system 22 which contains a neural network 25 and may be connected other data storage or processing systems. During the interventional procedure, the second component 11, as shown in FIG. 1B, may include a biopsy system 18, a LINAC system used for radiation therapy, or a surgical or interventional system. The biopsy system 18 represents an interventional component that can be also a radiation therapy system, a surgical interventional system, or another medical interventional component. The biopsy system 18 may be guided by images obtained via the MR imaging system 12 in combination with images obtained via the ultrasound imaging system 14. In certain embodiments, instead of a biopsy system, the system 11 may include a therapy system, such as a LINAC system used for radiation therapy or a surgical intervention or medical intervention system. It should be noted that the system and process described entails two stages in the biopsy procedure or interventional procedure, a pre-biopsy stage (e.g., patient-specific planning stage) where simultaneous MR and ultrasound imaging occurs, and an actual biopsy stage or procedure (e.g., interventional/therapy phase) where ultrasound imaging and needle insertion occurs. This is seen in FIG. 1B, where the display 26, processor 24, memory 22, and network interface 25 in system controller block 20 may be the same as used during the MR and ultrasound procedure or a different system block that allows the same functionality as system controller block 20.

The combined MR and ultrasound imaging system 10 may further include a system controller block 20 communicatively coupled to the other elements of the combined MR and ultrasound imaging system 10, including the MR imaging system 12, the ultrasound imaging system 14, and the therapy system 18. The controller 20 may include a memory 22 and a processor 24. In some embodiments, the memory 22 may include one or more tangible, non-transitory, computer-readable media that store instructions executable by the processor 24 and/or data to be processed by the processor 24. For example, the memory 22 may include random access memory (RAM), read only memory (ROM), rewritable non-volatile memory such as flash memory, hard drives, optical discs, and/or the like. Additionally, the processor 24 may include one or more general purpose microprocessors, one or more application specific processors (ASICs), one or more field programmable logic arrays (FPGAs), or any combination thereof. Further, the memory 22 may store instructions executable by the processor 24 to perform the methods described herein. Additionally, the memory 22 may store images obtained via the MR imaging system 12 and the ultrasound imaging system 14 and/or algorithms utilized by the processor 24 to help guide the therapy system 18 based on image inputs from the MR imaging system 12 and the ultrasound imaging system 14, as discussed in greater detail below. The memory 22 may also store a neural network 25 that when trained functions as an unsupervised deep learning-based deformable registration network as described in greater detail below. In certain embodiments, the system 10 may be coupled to a remote database that includes the network 25. Further, the controller 20 may include a display 26 that may be used to display the images obtained by the MR imaging system 12 and the ultrasound imaging system 14.

It should be noted that the types of MR and ultrasound images acquired may vary. For efficiency and also to match acquisition frame rates, one embodiment has two-dimensional (2D) MR images acquired simultaneously with three-dimensional (3D) ultrasound images over time, i.e., matching time-series 2D MR images to time-series 3D ultrasound images at each time point. In this case, there is the possibility that endogenous fiducial structures/markers in the time-series 3D ultrasound images may not be common to the time-series 2D MR images. In certain embodiments, the MR images and/or ultrasound images may be stacked 2D images acquired over time.

Alternatively, sorting the time-series 2D MR images into corresponding collections, with each collection representing the same respiratory state, reformatted time-series 3D (4D) MR images that are temporally matched with the time-series 3D (4D) ultrasound images may be generated. This increases the probability that endogenous fiducial structures/markers in the ultrasound images are common in the MR images. However, even if this is not the case, the techniques disclosed below provide adequate matching or registration between MR and ultrasound images. In another embodiment, with sufficiently fast acquisition speeds, time-series 3D (4D) MR images are acquired simultaneously with time-series 3D (4D) ultrasound images to yield corresponding time-series 3D volume images that are temporally matched. As an MR image set at a reference time point and the corresponding ultrasound image volume are acquired at the same time point, the organ-of-interest visualized in MR and ultrasound have the same shape, orientation, and feature outlines, making the MR-to-ultrasound transformation an easier undertaking.

Figure 2:
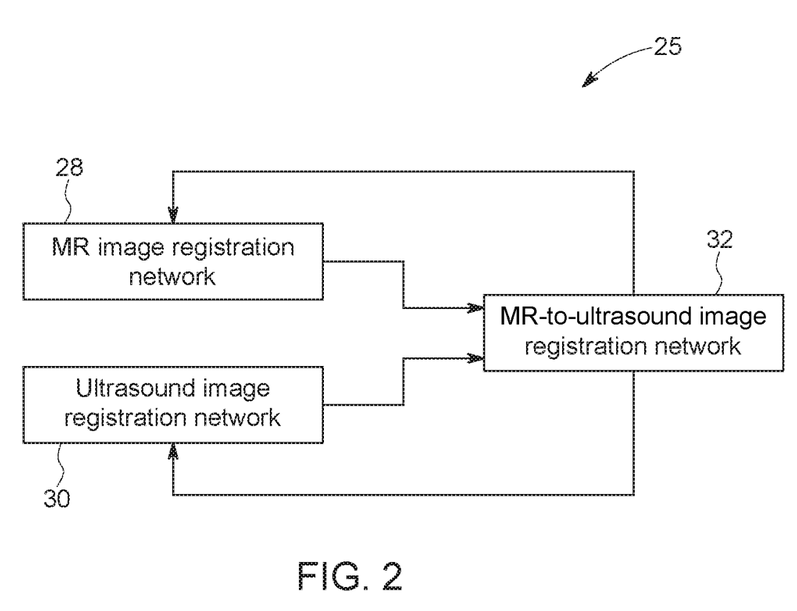
FIG. 2 illustrates a schematic diagram of an embodiment of a neural network, in accordance with aspects of the present disclosure.

FIG. 2 illustrates a schematic diagram of an embodiment of the neural network 25 (e.g., unsupervised deep learning-based deformable registration network). The network 25 provides a fast deformable registration framework for general intervention/therapy applications where MR and ultrasound are used complementarily. In particular, as described in greater detail below, endogenous fiducial markers (e.g., objects) are registered within the same imaging modality (e.g., ultrasound-to-ultrasound or MR-to-MR). The neural network 25 is trained to restrict the space of possible deformations and transformations of a specific anatomy-of-interest. For example, the neural network 25 determines the space of deformation and transformation in position, shape, orientation, and/or size of an anatomical structure as a function of physiological motion. The neural network 25, in conjunction with a physics-based model) enables a more efficient technique for performing accurate registration. In addition, the neural network 25 (and physics-based model) enables a more efficient technique for determining deformation and transformational fields or vectors that are then applied to images acquired from using a different imaging modality even if the image contrast and/or spatial resolution varies.

The network 25 includes an MR image registration network or subnetwork 28 and an ultrasound image registration network or subnetwork 30. As described below, the described embodiments include acquiring simultaneous MR images and ultrasound images in the planning phase as training data to train the neural network 25. The first set of ultrasound images is the reference set that is temporally linked to a corresponding MR image set. The MR images are utilized to train the MR image registration network 28 to determine MR-determined deformation and transformation fields or vectors (e.g., so that a position, a shape, an orientation, and a size of an object at a reference time point matches that of the same object at a different time). The ultrasound images are utilized to train the ultrasound image registration network to determine ultrasound-determined deformation and transformation fields or vectors (e.g., so that a position, a shape, an orientation, and a size of an object at a reference time point matches that of the same object at a different time). Each subnetwork 28, 30 minimizes the registration error of its respective input (e.g., image pairs). The network 25 also includes an MR-to-ultrasound image registration network or subnetwork 32. The temporally linked MR and ultrasound images (i.e., the MR and ultrasound images at each time point) are utilized to train the MR-to-ultrasound image registration network 32 to determine MR-to-ultrasound deformation and transformation fields or vectors (e.g., secondary deformation and transformation fields or vectors). The MR-to-ultrasound deformation and transformation fields or vectors are utilized as input to the subnetworks 28, 30 to enforce consistency between the deformation and transformation fields or vectors determined by each subnetwork 28, 30. The deformation consistency constraint can be based on a range of prior information, e.g., shape statistics of delineated regions of interest and surrounding anatomical structures based on past data, mechanical properties of tissues in ROI, confidence levels of deformation field estimates from each modality based on their image quality levels, etc. The initial affine transformation matrix to transform between planning MR and ultrasound images, and another transformation to register the planning ultrasound image and the first ultrasound image in intervention phase can be concatenated and used to transform the deformation from MR to ultrasound image space where we enforce the consistency of the deformations estimated based on MR and ultrasound images separately.

The consistency enforcing component (i.e., subnetwork 32) can be understood as similar to the discriminator in Generative Adversarial Networks (GAN) where synthetic samples generated by the generator is examined by the discriminator to determine if it is classified as either good or bad. In disclosed embodiments, the consistency-enforcing component performs a similar function. The deformation generated by the ultrasound-to-ultrasound sub-network 30 is examined by the consistency enforcing component by comparing with the deformation generated by the MR-to-MR sub-network 28.

In certain embodiments, a physics-based model (e.g., of the anatomy-of-interest such as the prostate) may add a constant or regularization on the deformation field. In particular, the physics-based model decreases the degrees of freedom available and determines what are allowable deformation/transformations. For deformations that have not been observed in the planning phase, as with a needle insertion for biopsy, physics-based models of allowable deformations/transformations may be utilized to simulate the process and generate synthetic images to represent this type of deformations in the training dataset. By doing this, the trained network can predict various deformations from patient's breathing and movement to needle insertion to achieve accurate registration result.

Subsequent to training, in the treatment/interventional phase, the trained network 25 takes a pair of ultrasound images as input and predicts the deformation/transformation field or vectors in real-time. The second set of ultrasound images is the volume data set acquired at the current time during the interventional/therapy phase. By predicting the deformation/transformation field or vectors in real-time using just ultrasound images, the same deformation/transformation field or vectors are then applied to the reference MR image set such that the new MR image set (with the applied deformation/transformation field or vectors) is a good and accurate representation of the body or anatomical region at the current time (i.e., a more correct representation of the position, shape, orientation, and/or size of the anatomical structure of interest at the current time). As such, the correct position of the target lesion or tumor can be represented relative to the interventional/therapy device positions.

The display of previously-acquired MR images from the pre-interventional MR+ ultrasound procedure (i.e., the planning stage) provides an accurate representation of the position, shape, and disposition of the organ-of-interest during the interventional procedure without having to acquire the MR images in real-time during the interventional procedure. As such, the interventional procedure can be performed in any appropriate location outside of the MR scanner. As described in greater detail, in certain embodiments, the disclosed techniques involve first determining a set of deformation and transformation vectors between MR images and ultrasound image volume at a reference point. Subsequently, the deformation and transformation vectors are determined between the ultrasound image volume at a reference time point in the pre-interventional procedure (intermediate set of deformation and transformation vectors), and the ultrasound image volume at some time point in the interventional procedure. Further, the second set of deformation and transformation vectors between time points of the ultrasound image volumes during the interventional procedure is determined. By exploiting the properties of a linear transformation process, transformed MR images may be displayed as a representation of the true position, shape, and orientation of the anatomy-of-interest and performing the interventional procedure using the transformed MR images for guidance.

As described below, this disclosure solves a general issue of registration of multi-modality images as well as images that have undergone deformable (affine) transformations. The techniques described in this disclosure solves the following scenarios. The generalized problem is to register an image(s) acquired at a prior time to an image(s) acquired at the current time where the change in the anatomy-of-interest may be due to physiologic motion or patient shifting. The objective is to register or match the MR images that have good soft tissue contrast and better delineation of the target lesion or tumor acquired during a planning phase to the real-time positional transformations during an interventional/therapy phase.

In a first scenario, endogenous fiducial markers visible and common in both MR and ultrasound images. In this case, let M(t) represent the MR image set (2D or 3D) at time, t. Let $U_p(t)$ represent the ultrasound image set (3D) at time, t. M(t) and Up(t) represent images acquired during the planning or pre-interventional phase. Similarly, let $U_T(t)$ represent ultrasound images acquired during the interventional phase. During the planning stage time-series MR and ultrasound images are acquired simultaneously such that each MR image, M(t) is matched temporally to an ultrasound volume data set, Up(t). Then, $\{M(t_1), M(t_2), \ldots, M(t_n)\}$ represents a times series of sets of MR images acquired at different time points during the planning phase, with a corresponding ultrasound time-series that are temporally matched, $\{U_p(t_1), U_p(t_2), \ldots, U_p(t_n)\}$. If it is assumed that images at $t=t_1$ are the reference or target images, the deformation and transformation fields or vectors (denoted by E(t) and Z(t) for the MR-to-MR, and ultrasound-to-ultrasound deformation and transformation to different time points, respectively), for each time point are $$E(t): M(t_1) \rightarrow M(t_m) \qquad (1)$$

and $Z(t): U_p(t_1) \rightarrow U_p(t_m)$ (2)

for some time point $t_m$. Note that implicit in this embodiment is that MR images with different image contrast to the time-series MR images may also be acquired. These being T1-weighted, T2-weighted, or some other parametric type image that contains image contrast that is preferred to view lesions or structures in the anatomy-of-interest. These lesions or structural contours are assumed to be transferred (via an intermediate transformation) to the time-series MR images, $\{M(t_1), M(t_2), \ldots, M(t_n)\}$, using known and established methods. As such, the deformation and transformation process described herein also transfers lesion or structural contours and are made available for image-guidance during the interventional procedure. This is indicated in the generalized MR data deformation network 42 (E*).

Since the time-series MR images may be 2D images and the time-series ultrasound images are 3D images or volumes, the same endogenous fiducial markers may or may not be visible in both image modalities. If the same endogenous fiducial markers are visible in both image modalities, then the deformation and transformation fields are equivalent, such that E(t)=Z(t).

Hence, during the interventional phase, at some time, t, the deformation and transformation field or vectors that match the ultrasound images at that time point to the reference or target images acquired during the planning or pre-interventional phase are determined in real-time, where:

$$Z'(t): U_p(t_1) \rightarrow U_T(t). \qquad (3)$$

Note that $t_1$ represents some reference time point selected in the pre-interventional or planning phase time-series ultrasound volume image set, $\{U_p(t)\}$. By matching Z'(t) to the available deformations and transformation fields or vectors determined during the planning phase, $\{Z(t_i)\}$, where i is some index, the corresponding deformation and transformation field or vector, $E(t_i)$ can be applied to the reference or target MR image, $M(t_1)$, to yield the MR image that represents the position of the target lesion or tumor at the current time, t, i.e., $M(t_i)$. This procedure, repeated at each time current point, t, then provides real-time imaging guidance using MR images that have good soft-tissue contrast and delineation of the target lesion or tumor. We note that the determination of the transformation, Z'(t), can be quickly determined by using the trained ultrasound-to-ultrasound deformation and transformation subnetwork 30 from the pre-interventional or planning phase for computational efficiency and to reduce the interventional procedure time.

Note that Z'(t) could be directly applied to the reference or target MR image, $M(t_1)$. However, differences in spatial resolution, and image contrast may yield some discordance between the deformation and transformation fields or vectors, E(t) and Z(t), necessitating the use of the corresponding deformation and transformation field or vectors specific to the MR images, E(t). The data consistency of the deformation/transformation can be checked by comparing E(t) and Z(t) at each time point.

In a second scenario, endogenous markers are not completely visible or common in both MR and ultrasound images. As the MR images may be primarily 2D, the endogenous fiducial markers in the 3D ultrasound images may not be present in the 2D MR images. Furthermore, differences in spatial resolution, and image contrast may yield some discordance between the deformation and transformation fields or vectors, E(t) and Z(t).

Under these circumstances, a further registration between pairs of MR and ultrasound images acquired at the same time need to be determined. The deformation and transformation field or vector between the pairs of MR and ultrasound images can be denoted by H(t), where $$H(t_i): M(t_i) \rightarrow U_p(t_i). \tag{4}$$

During the interventional, planning, or therapy phase, the deformation and transformation fields or vectors to register the reference or target ultrasound images, $U_p(t_1)$, to the current ultrasound images, $U_T(t_i)$, are determined as in equation (3). However, to correctly deform and transform the reference or target MR images, $M(t_1)$, the secondary and corresponding MR-to-ultrasound deformation and transformation field or vectors must also be applied. Hence, to arrive at the correct MR representation of the target lesion or tumor at the current time point during the interventional or therapy phase, $H(t_i)$ must first be applied to $M(t_i)$, followed by $Z'(t_i)$. That is:

$$Z'(t_i)\{H(t_i)\{M(t_i)\}\} = M_T(t_i). \tag{5}$$

In at third scenario, motion during the interventional phase and the planning phase is unmatched. There may be cases where the motion during the interventional or therapy phase cannot be matched to motion encountered during the planning phase. Under these circumstances, Z'(t) cannot be matched to set of deformation and transformation fields or vectors $\{Z(t_i)\}$ determined during the planning phase. As such, to correctly deform and transform the reference or target MR images, $M(t_1)$, the MR-to-ultrasound deformation for the reference or target time point is first determined. Note that this could be determined after image acquisition in the planning phase and before the intervention or therapy phase. Then, $$H(t_1): M(t_1) \rightarrow U_p(t_1). \tag{6}$$

The current ultrasound images acquired in the interventional or therapy phase is registered to the reference or target ultrasound images as in equation (3). Subsequently, the correct MR representation of the target lesion or tumor at the current time point during the interventional or therapy phase applies $H(t_1)$ to $M(t_1)$, followed by $Z'(t_i)$. That is:

$$Z'(t_i)\{H(t_1)\{M(t_1)\}\} = M_T(t_i) \tag{7}$$

The subsequent discussion teaches an efficient manner to calculate or determine the deformation and transformation fields or vectors (E(t), Z(t), H(t)) in real-time using neural networks and training datasets. In particular, in one embodiment, the training dataset for MR registration sub-network 28 is composed of pairs of MR images or volumes. For each pair of set of MR images, one image is designated as the "motion" image, the other one is set as target or reference image. The registration network 28 uses the idea of spatial transformer networks to sample and warp the "motion" image to the target/reference image, and minimizes a loss function that measures the dissimilarity between the warped "motion" image and the target/reference image. The ultrasound sub-network 30 works similarly with ultrasound images. The training dataset for both ultrasound and MR registration sub-networks 30, 28 are designed in the same way, the only difference being that there is no cross-modality registration, except to determine H(t). The training is performed on images within the same modality for images at different time points, and across images for different modalities for the same time point. Unlike supervised methods, the present techniques do not require knowledge of ground truth deformation fields between image pairs in the training dataset, which can be very onerous to generate.

In general, learning-based image registration, whether supervised or unsupervised, uses pairs of images in training that are generated by randomly sampling pairs of image/volume from the training dataset. This is to make sure all possible deformations and transformations of the anatomy-of-interest in the dataset are captured by random sampling, so the trained system can generalize to cope with possible unseen fiducial structures in images of the testing dataset. That is, $$E_i(t_m): M(t_i) \rightarrow M(t_m) \tag{8}$$

$$\text{and } Z_i(t_m): U_p(t_i) \rightarrow U_p(t_m), \tag{9}$$

where $E_i(t_m)$ and $Z_i(t_m)$ represent the random sampling of possible deformations and transformations between the ith time point as a reference or target, and some mth time point, $t_m$ for MR-to-MR and ultrasound-to-ultrasound images, respectively. The present techniques take advantage of simultaneous MR and ultrasound images that are temporally synchronized. In this way, the training image pairs acquired in the planning phase provide a range of spatial deformation/transformation estimates that are representative of those that will be observed in images acquired during the intervention phase. Particularly, if one assumes each patient has similar breathing patterns or other repetitive motion in both planning and intervention phases. However, the disclosed techniques enables deformation/transformation even if the motion or breathing pattern is not repetitive or reproducible between the planning phase and the interventional phase.

As noted above, for deformations that have not been observed in the planning phase, as with a needle insertion for biopsy, physics-based models of allowable deformations/transformations can simulate the process and generate synthetic images to represent this type of deformations in the training dataset. By doing this, the trained network can predict various deformations from patient's breathing and movement to needle insertion to achieve accurate registration result.

Another important component of the disclosed techniques is the fusion of time-synchronized MR and ultrasound information in the training process. This step is important and it differentiates the disclosed techniques from past techniques that are unable to verify or calibrate the ultrasound-based tracking or registration and, thus, cannot correct the error in the ultrasound-only registration. By leveraging the simultaneous MRI and ultrasound image acquisition in the planning phase, the disclosed techniques temporally match MRI and ultrasound image sets or volumes to enable better determination of the deformation/transformation field or vectors. Furthermore, by using the time-series ultrasound volume image set, a deformation/transformation subnetwork for the ultrasound images can be trained for that specific patient prior to the interventional procedure. This allows for a shorter interventional procedure time. This approach also customizes or personalizes the deformation/transformation network for the respirator, cardiac, or physiologic motion specific for that patient rather than using a generalized network that may introduce errors. For the first corresponding MR and ultrasound images, the disclosed techniques perform an affine registration to register them together, the affine transformation matrix is saved and will be used subsequently as a starting point to rapidly determine the other possible registrations (i.e., deformation and transformation fields or vectors).

In certain embodiments, one way to align or register MR and ultrasound images is to just register each pair of corresponding MR and ultrasound images, and then crop the co-registered MR and ultrasound images with the field-of-view size based on the overlap between the MR and ultrasound images. After applying above procedure repeatedly to each corresponding pair of MR and ultrasound images, a sequence of registered and cropped MR and ultrasound images are formed, which can be viewed as two-channel multimodal data. After this preprocessing step, a multimodal registration can then be performed. However, in this approach, the training system can only predict the deformation in the cropped image, thus, the entire image deformation is not available. Thus, in a preferred embodiment, the network architecture in FIG. 2 is utilized.

Figure 3:
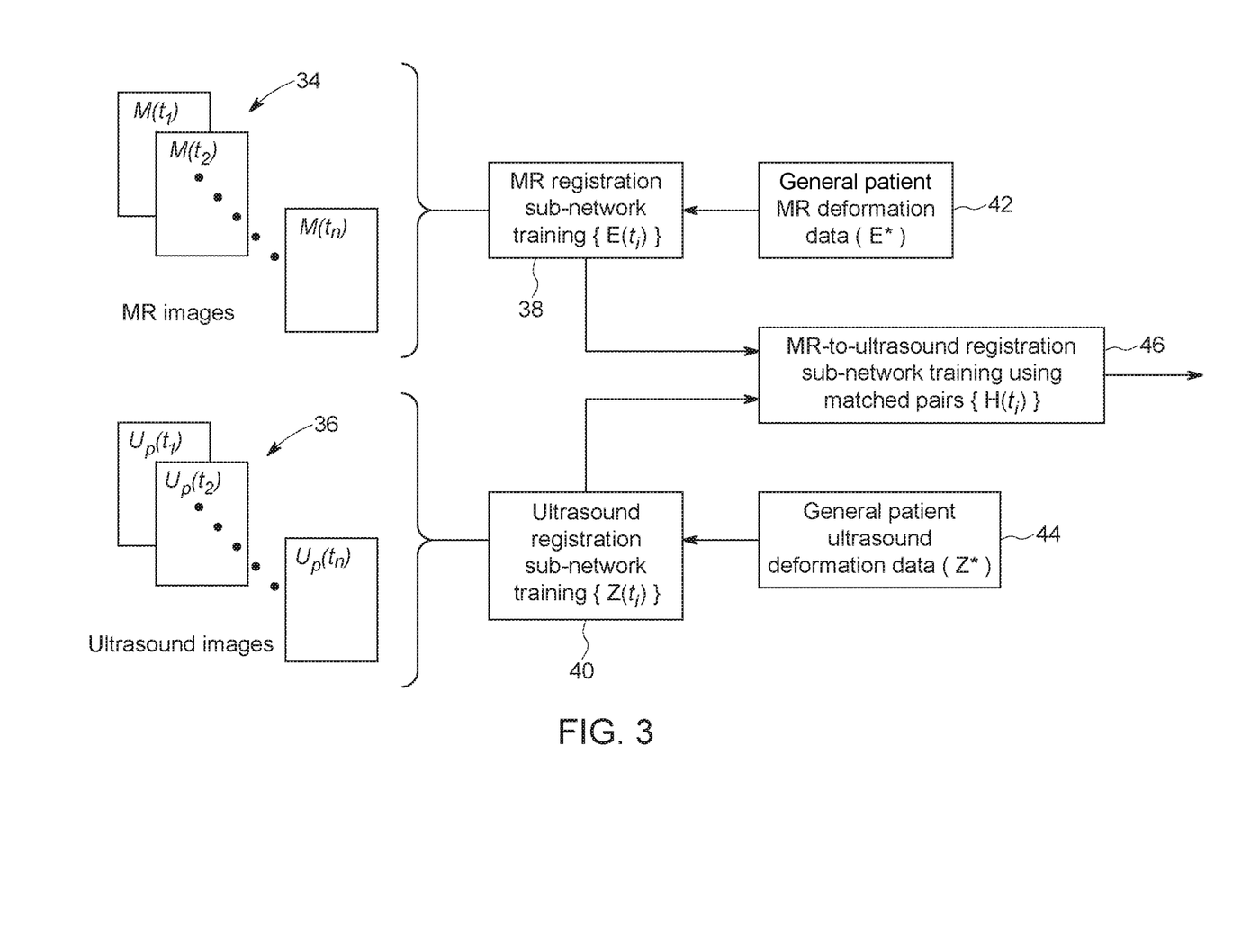
FIG. 3 illustrates a schematic diagram of an embodiment illustrating the training of the neural network of FIG. 2, in accordance with aspects of the present disclosure.

FIG. 3 illustrates a schematic diagram of an embodiment illustrating training of the neural network 25 of FIG. 2. FIG. 3 illustrates the inputs to the training of the different sub-networks during the patient-specific planning stage or phase. As depicted, a plurality of MR images 34 (e.g., times series MR image set) and a plurality of ultrasound images 36 (e.g., time-series ultrasound image set) acquired simultaneously over a scanned duration are provided as inputs for training. In particular, the plurality of MR images 34 are provided to the MR image registration subnetwork 28 for training of the subnetwork 28 to determine MR-determined deformation and transformation fields or vectors (as indicated in block 38). The plurality of ultrasound images 36 are provided to the ultrasound image registration subnetwork 30 for training of the subnetwork 30 to determine ultrasound-determined deformation and transformation field or vectors (as indicated in block 40). In certain embodiments, the MR deformation data 42 and ultrasound deformation data 44 may be provided as training input to the subnetworks 28, 30, respectively. As previously noted, each subnetwork 28, 30 minimizes the registration error of its own image pairs (i.e., between the reference or target image at a reference time point and another image at a different time point). The matched pair deformation and transformation fields or vectors are utilized to train the MR-to-ultrasound image registration network 32 (as indicated in block 46) to determine MR-to-ultrasound deformation and transformation fields or vectors (e.g., secondary deformation and transformation fields or vectors) or each time point. The MR-to-ultrasound deformation and transformation fields or vectors are utilized as input to the subnetworks 28, 30 to enforce consistency between the deformation and transformation fields or vectors determined by each subnetwork 28, 30 to provide a more accurate deformation and transformation from one time point to another.

Figure 4:
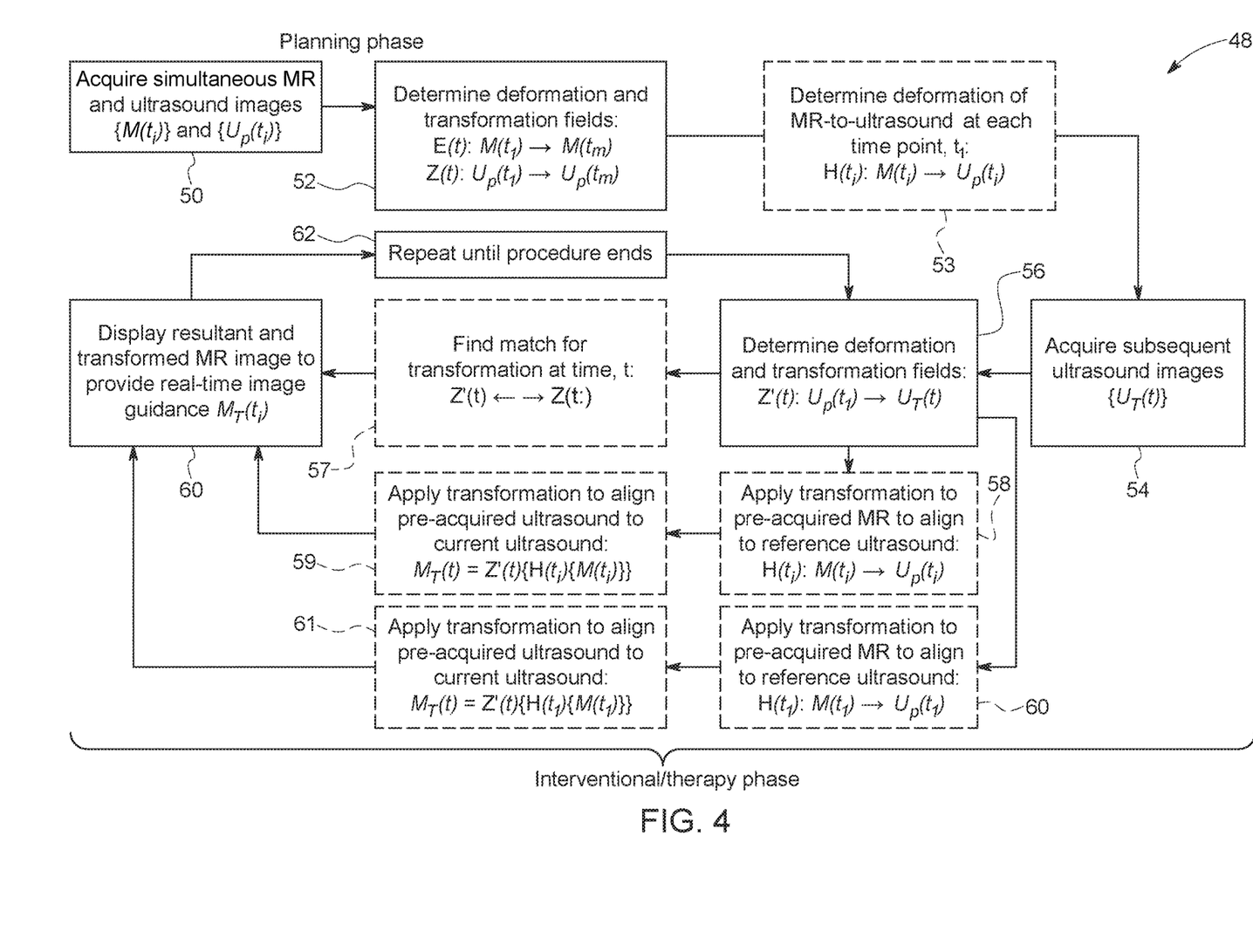
FIG. 4 illustrates a flowchart for an embodiment of a combined magnetic resonance and ultrasound image-guided interventional procedure, in accordance with aspects of the present disclosure.

FIG. 4 illustrates a flowchart of a method 48 of providing virtual real-time magnetic resonance images for direct imaging guidance of an interventional procedure (e.g., therapy or biopsy (e.g., prostate biopsy) of a patient. The method 48 consists of two stages of imaging: (1) a planning phase or pre-interventional stage (e.g., pre-biopsy or pre-therapy stage) (i.e., steps 50 to 53); and (2) an interventional/therapy phase or stage (e.g., biopsy stage) (steps 54 to 62). The steps of the planning stage may occur at any time before the interventional/therapy stage and may occur at a different location or the same location. For example, the planning stage may be conducted in the MR scanner and the interventional procedure (e.g., therapy or biopsy) may be performed outside the MR scanner, such as in a standard clinical examination room.

During the planning stage, in step 50, MR images (time-series ultrasound image set) and ultrasound images (e.g., time-series ultrasound image set) of a patient's anatomy-of-interest (e.g., prostate) are acquired simultaneously. In certain embodiments, one or more endogenous fiducial markers are identified in the ultrasound images at each time frame. For example, the endogenous fiducial markers may include blood vessels, the structural anatomy of the prostate, or the suspect lesion itself. In step 52, the neural network is trained utilizing the MR and ultrasound images to determine the respective deformation and transformation fields or vectors (e.g., MR-determined deformation and transformation fields or vectors and ultrasound-determined deformation and transformation fields or vectors) and MR-to-ultrasound deformation and transformation fields or vectors). In certain embodiments (e.g., the second and third scenarios discussed above), in step 53, the neural network is utilized to determine the deformation of MR-to-ultrasound at each time point, $t_1$. The second scenario being when endogenous markers are not completely visible or common in both MR and ultrasound images (and equation 5 is utilized). The third scenario being when motion during the interventional phase and the planning phase is unmatched (an equation 7 is utilized).

During the interventional/therapy stage, in step 54, ultrasound images (time-series ultrasound image set) of the patient's anatomy-of-interest (e.g., prostate) are acquired in real-time. In certain embodiments, the ultrasound images may be used to locate the same endogenous fiducial markers identified earlier. In step 56, at some time t, the deformation and transformation fields or vectors (e.g., secondary deformation and transformation fields or vectors) that match the ultrasound images at that time point to the reference or target ultrasound images acquired during the planning phase are determined in real-time.

In certain embodiments (e.g., the first scenario where endogenous fiducial markers visible and common in both MR and ultrasound images), in step 57, a match for transformation at time, t, is found (e.g., $Z(t)\kappa \rightarrow Z(t_i)$). In step 62, the transformed MR image representative (e.g., having the correction transformation) of the current time point is displayed to provide real-time guidance of the interventional procedure.

Alternatively, in certain embodiments (e.g., the second scenario), in step 58, the MR-to-ultrasound deformation and transformation fields or vectors are applied to the previously acquired reference or target MR images (corresponding to the temporally linked target or reference ultrasound images) to align it to the reference ultrasound. In step 59, the secondary deformation and transformation fields or vectors are applied to align pre-acquired ultrasound to the ultrasound at the current time point to generate the transformed MR image that represents the anatomy-of-interest (e.g., pancreas) at the current time point. In step 62, the transformed MR image representative (e.g., having the correction transformation) of the current time point is displayed to provide real-time guidance of the interventional procedure.

In certain embodiments (e.g., the third scenario), in step 60, the MR-to-ultrasound deformation and transformation fields or vectors are applied to the previously acquired reference or target MR images (corresponding to the temporally linked target or reference ultrasound images) to align it to the reference ultrasound. In step 61, the secondary deformation and transformation fields or vectors are applied to align pre-acquired ultrasound to the ultrasound at the current time point to generate the transformed MR image that represents the anatomy-of-interest (e.g., pancreas) at the current time point. In step 62, the transformed MR image representative (e.g., having the correction transformation) of the current time point is displayed to provide real-time guidance of the interventional procedure. During the interventional procedure, in step 62, one or more of steps 54 to 61 may be repeated until the procedure ends.

Technical effects of the disclosed embodiments include providing systems and methods for providing real-time deformable registration to utilize in real-time image guidance of an interventional procedure that is faster, more accurate, and robust. In particular, an unsupervised deep learning-based deformable registration network is trained (on both MR and ultrasound images) and utilized to significantly increase computational speed to enable processing of ultrasound images in real-time and to enable real-time deformable registration. The unsupervised deep learning-based deformable registration network also includes multiple registration networks and a consistency enforcing component to minimize registration errors.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for providing real-time image guidance for an interventional procedure comprising:
   prior to the interventional procedure:
   acquiring simultaneously a time-series magnetic resonance (MR) image set and a first time-series ultrasound image volume set in an MR imaging scanner from a patient that are matched at each time point;
   matching each MR image in the time-series MR image set in time to a corresponding ultrasound image volume in the first time-series ultrasound image set;
   performing an intermediate transformation to transfer lesion or structural anatomy contours acquired with other MR image contrast acquisition techniques to the time-series MR image set to complement the structural anatomical information available in the time-series MR image set;
   for both the times series MR image set and the first times series ultrasound image volume set, respectively utilizing an MR image and a corresponding ultrasound image volume at some time point as a reference point in a respective MR reference image set and an ultrasound reference image volume set, calculating a respective first set of deformation and transformation vectors such that a position, a shape, an orientation, and a size of the object at the reference point matches that of the same object at a different time;
   and during the interventional procedure:
   acquiring a second time-series ultrasound image set such that at each time point the ultrasound images depict deformation of an anatomy-of-interest of the patient as it varies in position, shape, orientation, or size over time;
   utilizing the second time-series ultrasound image set, calculating a second set of deformation and transformation vectors between the ultrasound images of the anatomy-of-interest at the current time point and the ultrasound images of the ultrasound reference image set at the reference point;
   applying the first and second sets of deformation and transformation vectors to the previously acquired MR images of the time-series MR image set to generate transformed MR images;
   displaying the transformed MR images as a representation of the true position, shape, and orientation of the anatomy-of-interest; and
   performing the interventional procedure using the transformed MR images for guidance.

2. The method of claim 1, wherein the time-series MR image sets and the first time-series ultrasound image sets are two-dimensional images acquired at different time points, three-dimensional images acquired at different time points, or stack of two-dimensional images acquired at different time points.

3. The method of claim 1, comprising providing the first set of deformation and transformation vectors that are determined in the pre-interventional treatment phase during the simultaneous MR and ultrasound acquisition as an input to the training of a neural network that determines the space of deformation and transformation in position, shape, orientation, or size of an anatomical structure as a function of physiologic motion.

4. The method of claim 3, wherein during the interventional procedure, the trained neural network is configured to rapidly determine the deformation and transformation vectors that characterize the change in position, shape, orientation, or size of the anatomical structure from a reference state or time point.

5. The method of claim 4, comprising providing deformations and transformations from other patients as additional input for training the neural network.

6. The method of claim 1, wherein utilizing the ultrasound images that depict deformation of the anatomy-of-interest as it varies in position, shape, orientation, or size over time, provides a physical allowable range of motion of that anatomy-of-interest thereby speeding up the determination of the deformation and transformation vectors from the reference time point for any time point.

7. The method of claim 1, wherein prior to the interventional procedure, deformation and transformation vectors for both the MR images and ultrasound images are calculated independently for a given anatomical structure, and used as an internal check of the precision and accuracy of the calculation.

8. The method of claim 7, comprising, when there is disagreement between the ultrasound-determined and MR-determined deformation and transformation vectors, applying the MR-determined deformation and transformation vectors to the MR images at the reference time point to generate the transformed MR images that are a more correct representation of the position, shape, orientation, or size of the anatomical structure of interest at the current time point.

9. The method of claim 1, wherein applying the first and second sets of deformation and transformation vectors to the previously acquired MR images to generate the transformed MR images comprises:
   applying the first set of deformation and transformation vectors to the previously acquired MR images representing the anatomy-of-interest at a reference or target time point; and
   subsequently applying the second set of deformation and transformation vectors to generate the transformed MR images.

10. An interventional guidance system comprising:
    a memory encoding processor-executable routines;
    a processing component configured to access the memory and to execute the processor-executable routines, wherein the routines, when executed by the processing component, cause the processing component to:

receive a plurality of magnetic resonance (MR) images and a first plurality of ultrasound images of an anatomical region of a subject that were acquired simultaneously over a scanned duration prior to an interventional procedure;

utilize the first plurality of ultrasound images and their corresponding MR images from the plurality of MR images to determine a MR-to-ultrasound transformation, and, then train an unsupervised deep learning-based deformable registration network to generate deformation and transformation vectors between ultrasound images from the plurality of ultrasound images from two time points to obtain an MR-to-ultrasound mapping via the deformation and transformation vectors and the MR-to-ultrasound transformation;

during the interventional procedure, receive a second plurality of ultrasound images of the anatomical region of the subject;

utilize the trained unsupervised deep-learning based deformable registration network to determine secondary deformation and transformation vectors of the anatomical region between ultrasound images from the second plurality of ultrasound images at a current time point and reference ultrasound images from the first plurality of ultrasound images, to apply the deformation and transformation vectors to a reference MR image from the plurality of MR images, and to subsequently apply the secondary deformation and transformation vectors to the reference MR image to generate a transformed MR image representative of the anatomical region at the current time point; and display the transformed MR image during the interventional procedure.

11. The interventional guidance system of claim 10, wherein the processing component is configured to independently train the unsupervised deep learning-based deformable registration network to generate MR-specific deformation and transformation vectors based on the plurality of MR images and to generate ultrasound-specific transformation vectors based on the plurality of ultrasound images.

* * * * *